US012783882B2

(12) United States Patent
Baumel et al.

(10) Patent No.: US 12,783,882 B2
(45) Date of Patent: Nov. 3, 2026

(54) SYSTEM AND METHOD FOR GENERATING TRAINING DATA

(71) Applicant: Microsoft Technology Licensing, LLC, Redmond, WA (US)

(72) Inventors: Tal Baumel, Tel-Aviv (IL); Aaron Toby Bornstein, Zikhron Yaakov (IL); Antonio Andre Monteiro Manoel, Santos (BR); Huseyin A Inan, Sammamish, WA (US); Robert A. Sim, Bellevue, WA (US); Hadas Bitran, Ramat Hasharon (IL)

(73) Assignee: Microsoft Technology Licensing, LLC, Redmond, WA (US)

( * ) Notice: Subject to any disclaimer, the term of this patent is extended or adjusted under 35 U.S.C. 154(b) by 457 days.

(21) Appl. No.: 18/414,138

(22) Filed: Jan. 16, 2024

(65) Prior Publication Data

US 2025/0232170 A1 Jul. 17, 2025

(51) Int. Cl.
*G06N 3/08* (2023.01)
*G16H 10/60* (2018.01)

(52) U.S. Cl.
CPC ............... *G06N 3/08* (2013.01); *G16H 10/60* (2018.01)

(58) Field of Classification Search
CPC ................................ G06N 3/08; G16H 10/60
See application file for complete search history.

(56) References Cited

U.S. PATENT DOCUMENTS

| | | | | |
|---|---|---|---|---|
| 11,977,550 | B1 * | 5/2024 | Aptekar | G16H 10/60 |
| 2021/0303725 | A1 * | 9/2021 | Hartman | G06F 21/6245 |
| 2021/0342552 | A1 * | 11/2021 | Mishra | G06N 3/09 |
| 2024/0105296 | A1 * | 3/2024 | Fu | G06F 40/279 |

OTHER PUBLICATIONS

"Clinical software to unify healthcare data", Retrieved from: https://health.google/caregivers/care-studio/, Retrieved Date: Jul. 16, 2023, 6 Pages.

Fekete, Ágnes, "Synthetic healthcare data platform for pharmaceuticals, research, and patient care", Retrieved from: https://mostly.ai/healthcare-data-platform, Mar. 30, 2023, 16 Pages.

* cited by examiner

*Primary Examiner* — Kenneth B Lee, Jr.
(74) *Attorney, Agent, or Firm* — Foley IP Law, PLLC

(57) ABSTRACT

A method, computer program product, and computing system for: accessing a first siloed dataset concerning one or more medical notes; processing the first siloed dataset to identify clinical items within the one or more medical notes, thus defining a first tagged clinical item set; selecting a first set of templates for the first siloed dataset based, at least in part, upon the first tagged clinical item set within the first siloed dataset; defining a first instruct dataset for the first siloed dataset based, at least in part upon the first set of templates and first tagged clinical item set; and training a generative model using the first instruct dataset, thus defining a generative model trained for the first siloed dataset.

20 Claims, 3 Drawing Sheets

SYSTEM AND METHOD FOR GENERATING TRAINING DATA

TECHNICAL FIELD

This disclosure relates to generative AI systems and, more particularly, to the generation of training data for generative AI models.

BACKGROUND

Generative models are a class of machine learning models designed to generalize over input data to create new data similar to the input data they were trained on. These models have gained significant attention for their ability to produce realistic and novel outputs in various domains, including images, text, and audio. They operate by learning the underlying patterns and structures of the training data, enabling them to generate new, synthetic data that resembles the original dataset.

Despite their remarkable capabilities, training generative models becomes challenging when dealing with data containing Personally Identifiable Information (PII) and is subject to contractual restrictions. These models learn the intricate details of the training data, which might inadvertently capture and reproduce sensitive information, potentially violating privacy regulations and contractual obligations. Balancing the ethical and legal implications of handling PII with the advancement of generative models requires careful consideration, robust anonymization techniques, and adherence to data privacy laws and contractual agreements. Achieving this balance involves exploring innovative methodologies such as differential privacy, federated learning, or employing synthetic data generation to protect sensitive information while training effective and ethical generative models.

BRIEF DESCRIPTION OF THE DRAWINGS

Like reference symbols in the various drawings indicate like elements.

DETAILED DESCRIPTION OF THE PREFERRED EMBODIMENTS

Figure 1:
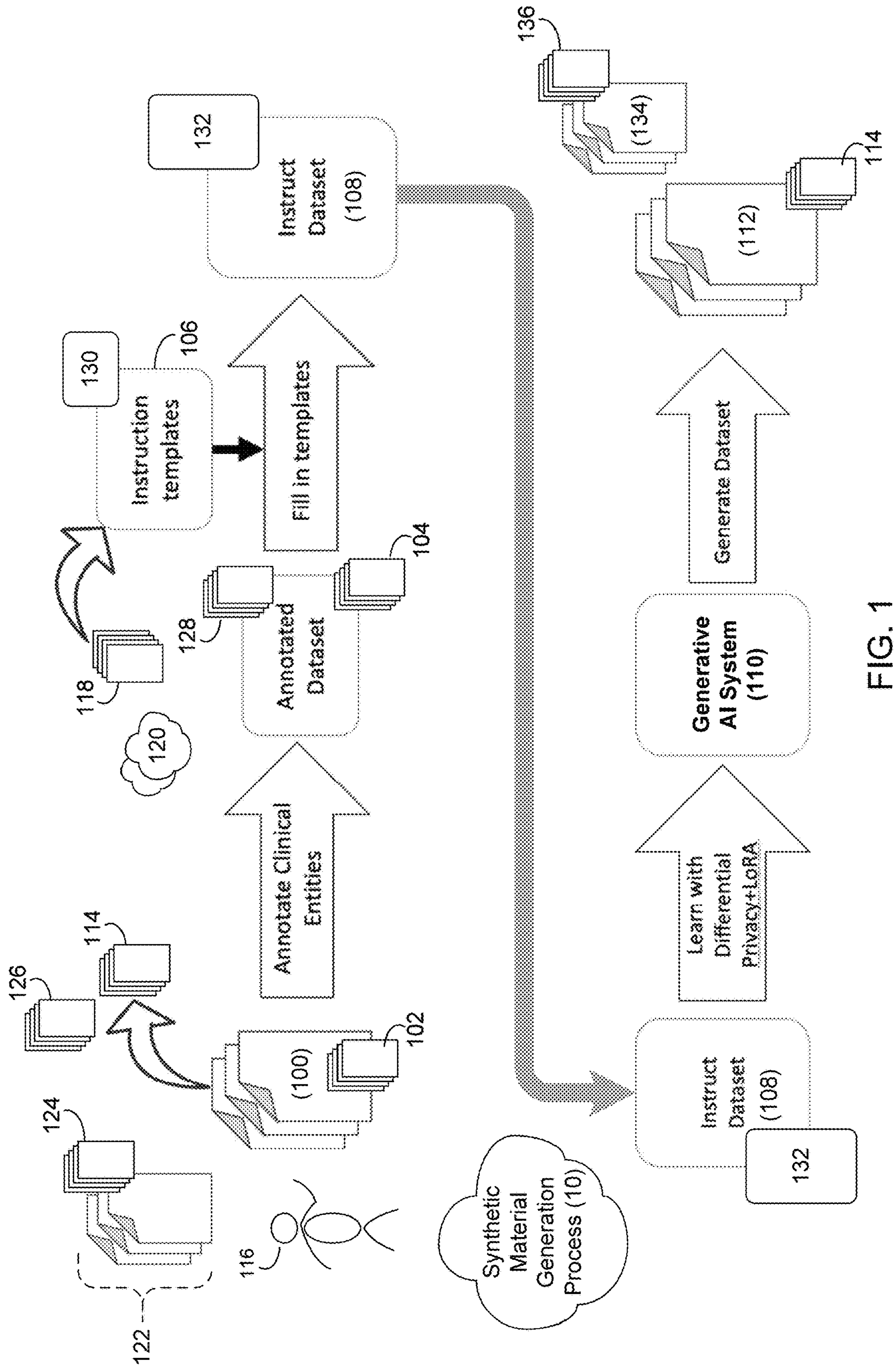
FIG. 1 is a diagrammatic view of a synthetic material generation process in accordance with various embodiments of the present disclosure.

Referring to FIG. 1 and as will be discussed in greater detail below, implementations of synthetic material generation process 10 may process siloed data (e.g., first siloed dataset 100) that includes medical notes (e.g., medical notes 102) to identify clinical items (e.g., first tagged clinical item set 104) within the medical notes (e.g., medical notes 102). A set of templates (e.g., first set of templates 106) may be selected based upon the identified clinical items (e.g., first tagged clinical item set 104). An instruct dataset (e.g., first instruct dataset 108) may be defined for the siloed data (e.g., first siloed dataset 100) based upon the selected set of templates (e.g., first set of templates 106) and the identified clinical items (e.g., first tagged clinical item set 104), thus allowing a generative model (e.g., generative model 110) to be trained using the instruct dataset (e.g., first instruct dataset 108).

Once trained for the siloed data (e.g., first siloed dataset 100), the generative model (e.g., generative model 110) may be used to generate a synthetic dataset (e.g., first synthetic dataset 112) based upon the siloed data (e.g., first siloed dataset 100), wherein the synthetic dataset (e.g., first synthetic dataset 112) is a data twin of the siloed data (e.g., first siloed dataset 100) that encompasses the spirit and style of the siloed data (e.g., first siloed dataset 100) while not having a 1:1 correspondence with the individual elements of the siloed data (e.g., first siloed dataset 100).

The details of one or more implementations are set forth in the accompanying drawings and the description below. Other features and advantages will become apparent from the description, the drawings, and the claims.

Figure 2:
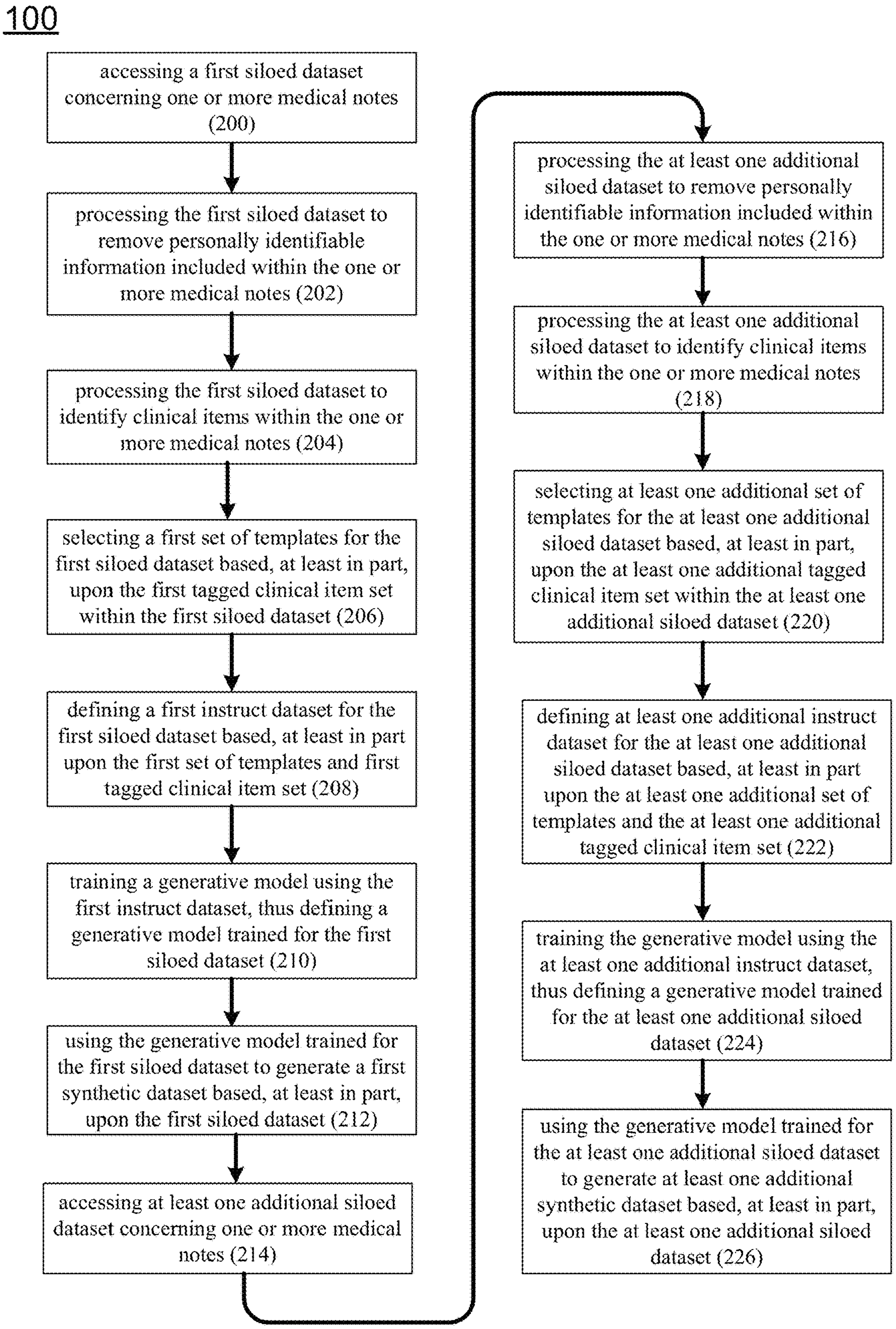
FIG. 2 is a flow chart of one implementation of the synthetic material generation process of FIG. 1 in accordance with various embodiments of the present disclosure.

Synthetic Material Generation Process:

Referring also to FIG. 2, synthetic material generation process 10 may access 200 a first siloed dataset (e.g., first siloed dataset 100) concerning one or more medical notes (e.g., medical notes 102). A siloed dataset (e.g., first siloed dataset 100) refers to a collection of data that is partitioned, isolated, or segregated, often intentionally, from other datasets or sources of information. When training a generative AI model, a siloed dataset refers to a scenario where the available data is compartmentalized, either due to organizational reasons, privacy concerns, access limitations, or regulatory constraints.

In the context of generative AI, a siloed dataset (e.g., first siloed dataset 100) can present challenges for training robust and accurate models. These challenges arise because the model's training heavily relies on the diversity and richness of the data it learns from. Siloed datasets (e.g., first siloed dataset 100) may lack the variety and depth necessary to capture the full range of patterns, nuances, and representations within a given domain.

For instance, if a generative AI model is only trained on a limited subset of data that doesn't encompass the full spectrum of variations or scenarios, the generated outputs might be biased, limited, or not representative of the entire dataset. This could lead to suboptimal performance, such as generating unrealistic or narrow outputs that don't reflect the true diversity of the domain.

Overcoming the limitations imposed by siloed datasets dataset (e.g., first siloed dataset 100) often involves finding ways to merge or access diverse data sources without violating privacy, confidentiality, or legal constraints. Techniques like federated learning (e.g., training models across decentralized datasets without exchanging them), synthetic data generation (e.g., creating artificial data that mirrors real data distribution), or differential privacy (e.g., adding noise to protect individual data points) might be employed individually or in concert to enrich the training dataset without directly accessing or combining the siloed information.

A medical note (e.g., medical notes 102) within a dataset (e.g., first siloed dataset 100) typically refers to a piece of documentation or record containing information related to a patient's medical history, examination details, diagnoses, treatments, prescriptions, and other relevant healthcare-related information. In the context of a dataset (e.g., first siloed dataset 100), a medical note (e.g., medical notes 102) represents a single entry or observation within a larger collection of such records or notes, forming part of a database used for various purposes, such as research, analysis, or training machine learning models in healthcare.

These medical notes (e.g., medical notes 102) could come from various sources within the healthcare system, including but not limited to:

- Physician's Notes: These contain detailed accounts of a patient's medical history, symptoms, physical examination findings, diagnoses, treatment plans, and prognosis as documented by a healthcare provider.
- Nursing Notes: Notes made by nurses, documenting patient care, vital signs, medication administration, and observations during a patient's hospital stay.
- Operative Reports: Detailed records of surgical procedures, outlining what was done during surgery, findings, and post-operative care instructions.
- Pathology Reports: Documents detailing findings from laboratory examinations of tissues, blood, or other samples, often used to diagnose diseases or conditions.

An example of a siloed dataset (e.g., first siloed dataset 100) that includes one or more medical notes (e.g., medical notes 102) may include a collection of data that was made available from e.g., a single healthcare system.

In the United States, there are numerous major healthcare systems, many of which operate across multiple states and have numerous hospitals, clinics, and medical facilities.

These healthcare systems often include multiple hospitals, specialty clinics, research centers, and academic institutions and they play a vital role in providing healthcare services, conducting medical research, and educating healthcare professionals in the United States.

When combined into a dataset (e.g., first siloed dataset 100), these medical notes (e.g., medical notes 102) contribute to a wealth of information that can be analyzed for research purposes, statistical analysis, or to train machine learning models. For instance, Natural Language Processing (NLP) models can be trained using these medical notes (e.g., medical notes 102) to extract relevant information, detect patterns, or assist in automating tasks such as coding diagnoses, suggesting treatment plans, or flagging potential health risks.

However, handling medical data requires strict adherence to patient privacy laws such as the Health Insurance Portability and Accountability Act (HIPAA) in the United States, the General Data Protection Regulation (GDPR) in the European Union, and other relevant regulations. Patient information in these medical notes (e.g., medical notes 102) is highly sensitive and should be anonymized or de-identified to prevent identification of individuals when used in research or shared for analysis purposes.

Accordingly, synthetic material generation process 10 may process 202 the first siloed dataset (e.g., first siloed dataset 100) to remove personally identifiable information (e.g., personally identifiable information 114) included within the one or more medical notes (e.g., medical notes 102).

Personally identifiable information 114 within medical data (e.g., first siloed dataset 100) includes any data or information that can be used to identify, contact, or locate an individual patient. In the context of medical records, personally identifiable information can encompass various sensitive details such as names, addresses, social security numbers, email addresses, phone numbers, and specific demographic information (e.g., date of birth, gender, race, or ethnicity). Any data that, when combined, can identify a specific person falls under personally identifiable information.

Removing personally identifiable information (e.g., personally identifiable information 114) from medical data (e.g., first siloed dataset 100) to allow its use as training material for a generative model (e.g., generative model 110) often involves a process called de-identification or anonymization. This process aims to protect individual identities while preserving the utility of the data (e.g., first siloed dataset 100) for research or analysis purposes.

Here are some common methods used to de-identify medical data:

- Data Masking or Redaction: This involves replacing or removing specific identifiable elements, such as names, addresses, or any other personal identifiers, by either blanking them out or replacing them with a generic placeholder.
- Pseudonymization: In this method, identifiers are replaced with artificial identifiers or pseudonyms, ensuring that the original identity of the individual cannot be easily ascertained. However, there should be a key or code that only authorized individuals possess to re-identify the information if necessary.
- Aggregation: Combining or aggregating certain data to ensure that specific individuals cannot be distinguished within the dataset. For instance, age might be represented in broader ranges rather than specific birthdates.
- Generalization: This involves altering specific details to a more general form. For example, instead of exact birthdates, using age ranges or months and years instead of exact dates.
- Tokenization: Replacing sensitive data with unique tokens or symbols, ensuring that the original information cannot be retrieved without access to the tokenization key.

When preparing medical data (e.g., first siloed dataset 100) for use in training generative models (e.g., generative model 110), it's essential to balance privacy protection with retaining the valuable information necessary for the model's learning. Care must be taken to comply with legal and ethical standards, ensuring that the de-identification process is robust enough to prevent re-identification while preserving the integrity and usefulness of the dataset (e.g., first siloed dataset 100) for training purposes.

For this example, assume that the first siloed dataset (e.g., first siloed dataset 100) is a siloed dataset from a healthcare system (generally) and from the general practitioner portion of the healthcare system (specifically). Accordingly, the medical notes (e.g., medical notes 102) included within the first siloed dataset (e.g., first siloed dataset 100) may concern the various type of ailments for which a patient visits a general practitioner, examples of which may include but are not limited to headaches, backaches, abdominal issues, sore joints, muscle pain, etc.

As it is likely that synthetic material generation process 10 already processed 202 the first siloed dataset (e.g., first siloed dataset 100) to remove personally identifiable information (e.g., personally identifiable information 114) included within the one or more medical notes (e.g., medical notes 102), none of the information within the first siloed dataset (e.g., first siloed dataset 100) is personally identifiable information (as it had already been removed).

Synthetic material generation process 10 may process 204 the first siloed dataset (e.g., first siloed dataset 100) to identify clinical items within the one or more medical notes (e.g., medical notes 102), thus defining a first tagged clinical item set (e.g., first tagged clinical item set 104).

Clinical items (e.g., first tagged clinical item set 104) within medical notes (e.g., medical notes 102) represent specific information related to a patient's medical history, symptoms, diagnoses, treatments, and observations documented by healthcare professionals. In the context of AI processing, these clinical items (e.g., first tagged clinical item set 104) are essential for training machine learning models, especially in healthcare-related tasks.

Some examples of clinical items found within medical notes may include but are not limited to:

Diagnoses and Medical Conditions: Information regarding specific diseases, health conditions, or syndromes the patient has been diagnosed with, such as diabetes, hypertension, asthma, or cancer.

Medications and Treatments: Details about prescribed medications, dosage, frequency, and duration of treatment, as well as information about surgeries, procedures, or therapies undergone by the patient.

Symptoms and Clinical Observations: Records of symptoms experienced by the patient, clinical signs observed during examinations, and subjective complaints, such as fever, pain, nausea, or shortness of breath.

Vital Signs and Measurements: Data related to vital signs including blood pressure, heart rate, temperature, respiratory rate, and other physiological measurements.

Laboratory Test Results: Reports from various lab tests, including blood tests, urine analyses, imaging results (X-rays, MRIs, CT scans), pathology reports, and other diagnostic investigations.

Procedures and Surgeries: Information about medical procedures, surgical interventions, and post-operative care documented in the patient's medical records.

Family and Social History: Details about the patient's family medical history, lifestyle factors, social habits, and environmental exposures that might impact their health.

Allergies and Adverse Reactions: Information regarding allergies, sensitivities, or adverse reactions to medications or environmental factors.

AI processing of medical notes (e.g., medical notes 102) involves extracting, analyzing, and interpreting these clinical items (e.g., first tagged clinical item set 104). using various machine learning techniques. Natural Language Processing (NLP) models are often utilized to extract structured information from unstructured text, converting medical notes into structured data that can be used for decision support systems, predictive analytics, automated coding, or population health management. These AI models can assist healthcare professionals in tasks like disease prediction, outcome prognosis, treatment recommendations, and medical coding by utilizing the information contained within these clinical items.

Accordingly, the medical notes (e.g., medical notes 102) included within the first siloed dataset (e.g., first siloed dataset 100) may concern the various type of ailments for which a patient visits a general practitioner, examples of which may include but are not limited to headaches, backaches, abdominal issues, sore joins, muscle pain, etc.

Continuing with the example in which the first siloed dataset (e.g., first siloed dataset 100) is a siloed dataset from the general practitioner portion of a healthcare system, assume (for this simplified example) that the clinical items (e.g., first tagged clinical item set 104) within the medical notes (e.g., medical notes 102) include:

<SYMPTOM TYPE>

<SYMPTOM DURATION>

<SYMPTOM SEVERITY>

Synthetic material generation process 10 may select 206 a first set of templates (e.g., first set of templates 106) for the first siloed dataset (e.g., first siloed dataset 100) based, at least in part, upon the first tagged clinical item set (e.g., first tagged clinical item set 104) within the first siloed dataset (e.g., first siloed dataset 100). As discussed above, the first tagged clinical item set (e.g., first tagged clinical item set 104) within the first siloed dataset (e.g., first siloed dataset 100) may include <SYMPTOM TYPE>, <SYMPTOM DURATION> and <SYMPTOM SEVERITY>. Accordingly, synthetic material generation process 10 may select 206 a first set of templates (e.g., first set of templates 106) for the first siloed dataset (e.g., first siloed dataset 100) based, at least in part, upon first tagged clinical item set 104 that includes <SYMPTOM TYPE>, <SYMPTOM DURATION> and <SYMPTOM SEVERITY>.

Accordingly, the first set of templates (e.g., first set of templates 106) may include a template as follows:

Generate a clinical note about a patient having a <SYMPTOM TYPE> that has lasted for a <SYMPTOM DURATION> and has a severity of <SYMPTOM SEVERITY>.

The first set of templates (e.g., first set of templates 106) may be chosen from a plurality of predefined templates (e.g., plurality of predefined templates 118). For example, such plurality of predefined templates (e.g., plurality of predefined templates 118) may be manually generated by data scientists for use by synthetic material generation process 10. Additionally/alternatively, such plurality of predefined templates (e.g., plurality of predefined templates 118) may be automatically generated by one or more AI algorithms (e.g., AI algorithms 120) that e.g., examine the patterns of the data included within the one or more medical notes (e.g., medical notes 102) so that the plurality of predefined templates (e.g., plurality of predefined templates 118) may be automatically defined.

Synthetic material generation process 10 may define 208 a first instruct dataset (e.g., first instruct dataset 108) for the first siloed dataset (e.g., first siloed dataset 100) based, at least in part upon the first set of templates (e.g., first set of templates 106) and the first tagged clinical item set (e.g., first tagged clinical item set 104).

An instruct dataset (e.g., first instruct dataset 108) in the context of a generative model refers to a dataset that is specifically structured or designed to guide or instruct the generative model during its training process. This type of dataset could provide examples, or specific guidelines intended to shape the learning of the model, helping it generate outputs that align with those instructions.

For instance, in certain cases, when training a generative model, researchers or developers might curate a dataset with specific characteristics or examples to direct the model's learning process towards generating outputs that possess particular attributes or qualities. This instruct dataset (e.g., first instruct dataset 108) could include labeled examples or exemplars that the model is encouraged to emulate or specific guidelines for the type of outputs it should generate.

The aim of such instruct datasets (e.g., first instruct dataset 108) might be to steer the generative model towards producing outputs that meet certain criteria, adhere to defined styles, or align with predefined structures. This guidance could help ensure that the model generates outputs that possess desired qualities or characteristics.

For example, in image generation, an instruct dataset (e.g., first instruct dataset 108) might include images labeled as 'bright,' 'sunset scenes,' or 'landscapes.' By training a generative model on such a dataset, the model could be directed to produce images that align with these specific instructions, creating outputs with the desired features or styles.

Instruct datasets (e.g., first instruct dataset 108) can be a way to influence or guide the learning process of a generative model, providing a level of supervision to steer the model towards generating outputs that meet certain predefined criteria or styles.

Continuing with the example in which the first siloed dataset (e.g., first siloed dataset 100) is a siloed dataset from the general practitioner portion of a healthcare system and (for this simplified example) the first set of templates (e.g., first set of templates 106) includes the following template: Generate a clinical note about a patient having a <SYMPTOM TYPE> that has lasted for a <SYMPTOM DURATION> and has a severity of <SYMPTOM SEVERITY>, first instruct dataset 108 may include statistics concerning the medical notes (e.g., medical notes 102) within the first siloed dataset (e.g., first siloed dataset 100).

For example, assume that the first siloed dataset (e.g., first siloed dataset 100) includes 1,000,000 medical notes (e.g., medical notes 102). Further assume that within these 1,000,000 medical notes (e.g., medical notes 102), there are 30,000 medical notes concerning a moderate-severe headache for less than a week, 40,000 medical notes concerning a mild-moderate stomach ache for 1-2 weeks, and 25,000 medical notes concerning a mild backache for over 2 weeks.

Therefore, the instruct dataset (e.g., first instruct dataset 108) may be as follows:

Generate 30,000 clinical notes about a patient having a moderate-severe headache for less than a week;

Generate 40,000 clinical notes about a patient having a mild-moderate stomach ache for 1-2 weeks;

Generate 25,000 clinical notes about a patient having a mild backache for over 2 weeks;

Accordingly, synthetic material generation process 10 may train 210 a generative model (e.g., generative model 110) using the first instruct dataset (e.g., first instruct dataset 108), thus defining a generative model (e.g., generative model 110) trained for the first siloed dataset (e.g., first siloed dataset 100).

For example, synthetic material generation process 10 may provide first instruct dataset 108 that defines the following instructions:

Generate 30,000 clinical notes about a patient having a moderate-severe headache for less than a week; Generate 40,000 clinical notes about a patient having a mild-moderate stomach ache for 1-2 weeks;

and Generate 25,000 clinical notes about a patient having a mild backache for over 2 weeks.

The above example is simply for illustrative purposes and is not intended to be a limitation of this disclosure, as other configurations are possible and are considered to be within the scope of this disclosure. For example, the above instruct dataset (e.g., first instruct dataset 108) may be broken down into smaller portions (e.g., one for 30,000 clinical notes, one for 40,000 clinical notes, and one for 25,000 clinical notes). Accordingly, synthetic material generation process 10 may train 210 generative model 110 using first instruct dataset 108, thus defining a generative model (e.g., generative model 110) that was trained for first siloed dataset 100.

A generative AI model (e.g., generative model 110) refers to a type of artificial intelligence system designed to create or generate new data that resembles the examples it was trained on. Unlike discriminative models, which are used for classification tasks (like determining whether an image contains a cat or a dog), generative models (e.g., generative model 110) create new data points that are similar to the training dataset.

These models learn the underlying patterns and structures of the input data during the training process, enabling them to generate new, synthetic data. They have numerous applications in various domains, including:

Image Generation: Creating new, realistic images, such as faces, landscapes, or objects.

Text Generation: Writing articles, stories, or poems that resemble human-written text.

Data Augmentation: Generating synthetic data to increase the size and diversity of training datasets for various tasks.

Some popular types of generative models (e.g., generative model 110) include:

Generative Adversarial Networks (GANs): Consist of two neural networks—a generator and a discriminator—engaged in a game where the generator creates synthetic data, and the discriminator distinguishes between real and generated data. Over time, both networks improve their performance, resulting in more realistic generated data.

Variational Autoencoders (VAEs): Work by encoding input data into a lower-dimensional representation and then decoding it to generate new data samples. VAEs learn a probabilistic distribution of the input data and generate new samples by sampling from that distribution.

Transformers: Neural network architectures that consist in first transforming words into "tokens", and then processing these tokens using consecutive "attention" and feed-forward operations. Most large language models, such as BERT and GPT, can be considered transformers.

Synthetic material generation process 10 may use 212 the generative model (e.g., generative model 110) trained for the first siloed dataset (e.g., first siloed dataset 100) to generate a first synthetic dataset (e.g., first synthetic dataset 112) based, at least in part, upon the first siloed dataset (e.g., first siloed dataset 100), wherein the first synthetic dataset (e.g., first synthetic dataset 112) may include one or more synthetic medical notes (e.g., synthetic medical notes 114).

Synthetic data (e.g., first synthetic dataset 112) generated by a generative AI model (e.g., generative model 110) refers to artificially created data that mimics or resembles real data, produced by machine learning models specifically designed for this purpose. Generative models (e.g., generative model 110), such as Generative Adversarial Networks (GANs), Variational Autoencoders (VAEs), or Transformers, are used to create synthetic data that imitates the patterns and characteristics of the original dataset.

The process involves training these generative models (e.g., generative model 110) on a set of real data, allowing them to learn the underlying structures and correlations within the dataset. Once trained, the models can generate new data samples that are statistically similar to the original dataset but are not derived from actual observations or instances. Crucially, the training procedure must be differentially private, to further guarantee that nothing that is exclusive to any particular sample will be revealed in the synthetic data.

For instance:

Image Generation: A generative model trained on a dataset of human faces might produce new, synthetic faces that look realistic but don't correspond to any real individuals in the training data.

- Text Generation: Models trained on a corpus of text can generate new sentences, paragraphs, or articles that resemble human-written content but are entirely synthetic.

Synthetic data has several potential uses:

- Privacy Preservation: Generating synthetic data can be used to create substitutes for sensitive or private information, allowing analysis or research without revealing personal details.
- Data Augmentation: Creating additional data samples can expand the diversity and quantity of training data for machine learning models.
- Scenario Exploration: In certain industries like healthcare or finance, synthetic data can be used to simulate scenarios for testing or research without using real, potentially sensitive, or restricted data.

However, while synthetic data (e.g., first synthetic dataset 112) can be beneficial, it's crucial to validate its quality and applicability to the original data distribution. Generating accurate and representative synthetic data requires the generative models (e.g., generative model 110) to capture the essential patterns and variations present in the original dataset. Moreover, ensuring that the synthetic data (e.g., first synthetic dataset 112) doesn't introduce biases or diverge significantly from the original data's characteristics is crucial for its successful use in various applications.

As the generative model (e.g., generative model 110) was trained using first instruct dataset 108 that was developed based upon first set of templates 106 and first tagged clinical item set 104 included within medical notes 102 of first siloed dataset 100, the first synthetic dataset (e.g., first synthetic dataset 112) may be a data twin of the first siloed dataset (e.g., first siloed dataset 100) that encompasses the spirit and style of the of the first siloed dataset (e.g., first siloed dataset 100).

Additional Siloed Datasets:

Training a generative model (e.g., generative model 110) with diversified data is crucial to ensure that the model learns a comprehensive representation of the underlying patterns and variations within the dataset. Using diverse data helps in capturing the richness, complexity, and full spectrum of possibilities present in the domain it is meant to model.

There are several reasons why diversified data is essential for training a generative model:

- Generalization and Robustness: Diversified data helps the model generalize better to new, unseen data. If a generative model is trained only on a limited subset of examples, it might generate outputs that are biased, limited, or fail to represent the full range of possibilities in the domain. Exposure to varied data ensures the model is better equipped to handle diverse scenarios.
- Avoiding Overfitting: Overfitting occurs when a model learns the specific details and noise of the training data rather than the underlying patterns. Using diversified data helps prevent overfitting, as the model learns broader and more generalized representations that can apply to new examples beyond the training set.
- Increased Adaptability: Models trained on diverse data are more adaptable to different contexts or variations within the domain. This adaptability is crucial in real-world applications where data can come in various forms, conditions, or contexts.
- Reducing Bias and Assumptions: Exposure to diverse data can help reduce biases in the model's outputs. Biases might arise if the model only learns from a limited subset of the data, leading to skewed or inaccurate representations.
- Improved Creativity and Innovation: Generative models are often used in creative tasks like art generation or new content creation. Diverse training data can inspire creativity in the model, helping it produce novel, innovative outputs.
- Data Representativeness: Using a diverse dataset ensures that the model's outputs accurately represent the entire scope and variety of the domain it aims to model.

It's important to note that achieving diversity in training data while maintaining its quality and relevance is a balancing act. Simply adding vast amounts of data doesn't guarantee better performance. The quality, relevance, and representation of the data matter significantly, and the model should learn from a varied yet representative sample to ensure it generalizes well to unseen data while avoiding biases and overfitting.

Accordingly, it may be beneficial to train the generative model (e.g., generative model 110) on diverse datasets. Therefore, synthetic material generation process 10 may access 214 at least one additional siloed dataset (e.g., additional siloed dataset 122) concerning one or more medical notes (e.g., medical notes 124). These additional siloed datasets (e.g., additional siloed dataset 122) concerning one or more medical notes (e.g., medical notes 124) may include a collection of data that was made available from e.g., other healthcare systems As discussed above, synthetic material generation process 10 may process 216 the at least one additional siloed dataset (e.g., additional siloed dataset 122) to remove personally identifiable information (e.g., personally identifiable information 126) included within the one or more medical notes (e.g., medical notes 124).

As discussed above, synthetic material generation process 10 may process 218 the at least one additional siloed dataset (e.g., additional siloed dataset 122) to identify clinical items within the one or more medical notes (e.g., medical notes 124), thus defining at least one additional tagged clinical item set (e.g., at least one additional tagged clinical item set 128).

As discussed above, synthetic material generation process 10 may select 220 at least one additional set of templates (e.g., at least one additional set of templates 130) for the at least one additional siloed dataset (e.g., additional siloed dataset 122) based, at least in part, upon the at least one additional tagged clinical item set (e.g., at least one additional tagged clinical item set 128) within the at least one additional siloed dataset (e.g., additional siloed dataset 122).

As discussed above, synthetic material generation process 10 may define 222 at least one additional instruct dataset (e.g., at least one additional instruct dataset 132) for the at least one additional siloed dataset (e.g., additional siloed dataset 122) based, at least in part upon the at least one additional set of templates (e.g., at least one additional set of templates 130) and the at least one additional tagged clinical item set (e.g., at least one additional tagged clinical item set 128).

As discussed above, synthetic material generation process 10 may train 224 the generative model (e.g., generative model 110) using the at least one additional instruct dataset (e.g., at least one additional instruct dataset 132), thus defining a generative model (e.g., generative model 110) trained for the at least one additional siloed dataset (e.g., additional siloed dataset 122). For example, synthetic material generation process 10 may: a) train an independent model for the additional silo; or b) apply a federated learning technique to securely and jointly train one model across multiple silos. In the later scenario, synthetic material generation process 10 may generalize across multiple silos and generate a single synthetic dataset that characterizes all the silos.

As discussed above, synthetic material generation process 10 may use 226 the generative model (e.g., generative model 110) trained for the at least one additional siloed dataset (e.g., additional siloed dataset 122) to generate at least one additional synthetic dataset (e.g., at least one additional synthetic dataset 134) based, at least in part, upon the at least one additional siloed dataset (e.g., additional siloed dataset 122).

As discussed above, the at least one additional synthetic dataset (e.g., at least one additional synthetic dataset 134) may include one or more synthetic medical notes (e.g., one or more synthetic medical notes 136). wherein the at least one additional synthetic dataset (e.g., at least one additional synthetic dataset 134) may be a data twin of the at least one additional siloed dataset (e.g., additional siloed dataset 122) that encompasses the spirit and style of the of the at least one additional siloed dataset (e.g., additional siloed dataset 122).

As the instruct datasets (e.g., first instruct dataset 108 and/or at least one additional instruct dataset 132) are associated with individual siloed datasets (e.g., first siloed dataset 100 is associated with first instruct dataset 108 and/or additional siloed dataset 122 is associated with at least one additional instruct dataset 132), additional synthetic data may be generated at a future data for either of (in this example) first instruct dataset 108 and/or at least one additional instruct dataset 132. Accordingly, and once such synthetic data (e.g., at least one additional synthetic dataset 134 and/or first synthetic dataset 112) is generated, the corresponding original data (e.g., first siloed dataset 100 and/or additional siloed dataset 122, respectively) is generally no longer needed (thus mitigating any concerns about contractual obligations/limitations associated with the original data (e.g., first siloed dataset 100 and/or additional siloed dataset 122, respectively).

Accordingly, the instruct datasets (e.g., first instruct dataset 108 and/or at least one additional instruct dataset 132) may be used in conjunction with LoRA to fine-tune the generative model (e.g., generative model 110). As is known in the art, Low-Rank Adaptation of Large Language Models (LoRA) is a training method that accelerates the training of large models while consuming less memory. It adds pairs of rank-decomposition weight matrices (called update matrices) to existing weights, and only trains those newly added weights.

Low-Rank Adaptation of Large Language Models (LoRA) has several advantages:

- Previous pretrained weights are kept frozen so the model is not as prone to catastrophic forgetting.
- Rank-decomposition matrices have significantly fewer parameters than the original model, which means that trained LoRA weights are easily portable.
- LoRA matrices are generally added to the attention layers of the original model. Diffusers provides the load_attn_procs( ) method to load the LoRA weights into a model's attention layers. You can control the extent to which the model is adapted toward new training images via a scale parameter.
- The greater memory-efficiency allows you to run fine-tuning on consumer GPUs like the Tesla T4, RTX 3080 or even the RTX 2080 Ti.

Figure 3:
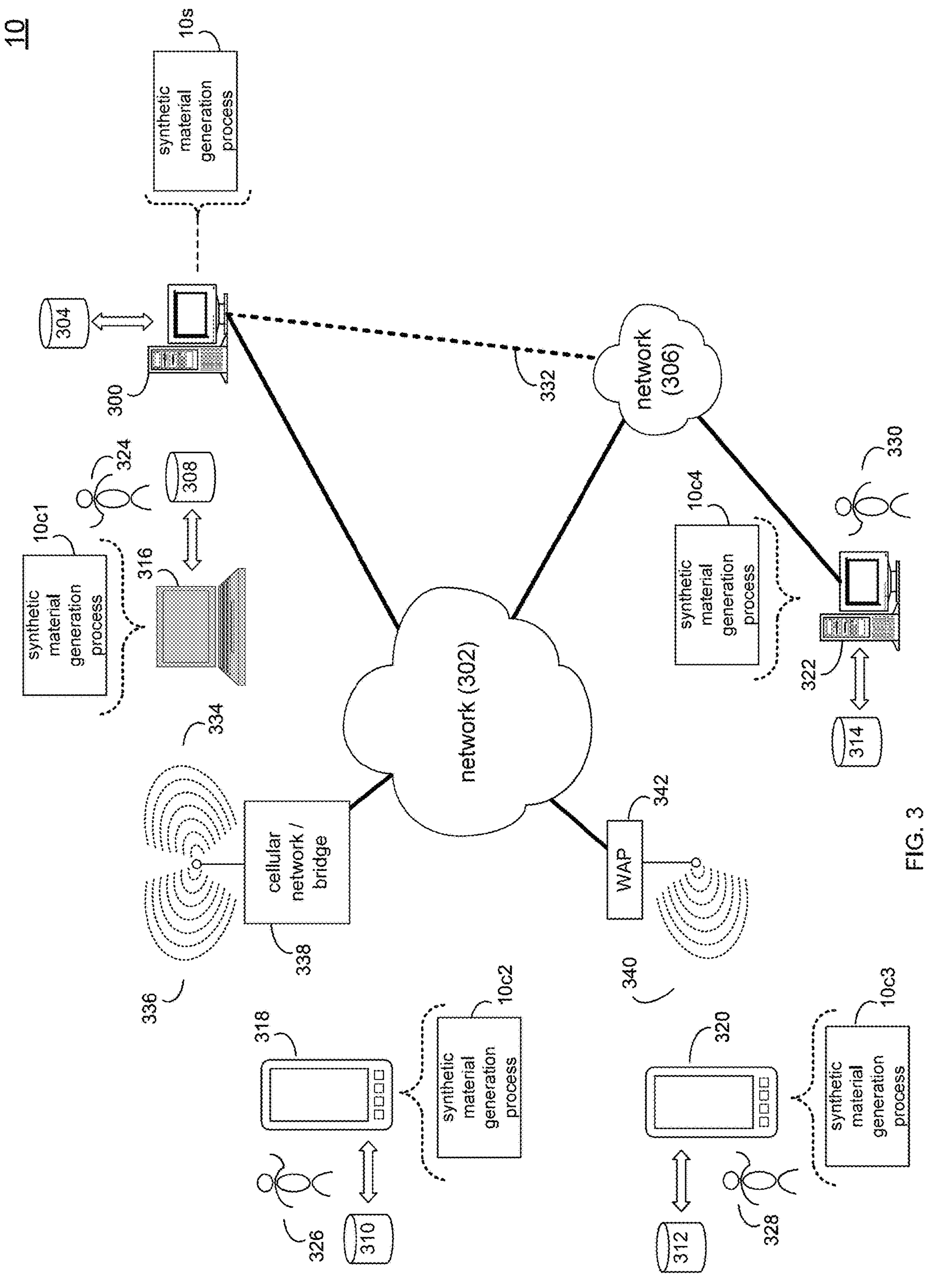
FIG. 3 is a diagrammatic view of a computer system and the synthetic material generation process of FIG. 1 coupled to a distributed computing network in accordance with various embodiments of the present disclosure.

System Overview:

Referring to FIG. 3, there is shown synthetic material generation process 10. Synthetic material generation process 10 may be implemented as a server-side process, a client-side process, or a hybrid server-side/client-side process. For example, synthetic material generation process 10 may be implemented as a purely server-side process via synthetic material generation process 10*s*. Alternatively, synthetic material generation process 10 may be implemented as a purely client-side process via one or more of synthetic material generation process 10*c*1, synthetic material generation process 10*c*2, synthetic material generation process 10*c*3, and synthetic material generation process 10*c*4. Alternatively still, synthetic material generation process 10 may be implemented as a hybrid server-side/client-side process via synthetic material generation process 10*s* in combination with one or more of synthetic material generation process 10*c*1, synthetic material generation process 10*c*2, synthetic material generation process 10*c*3, and synthetic material generation process 10*c*4.

Accordingly, synthetic material generation process 10 as used in this disclosure may include any combination of synthetic material generation process 10*s*, synthetic material generation process 10*c*1, synthetic material generation process 10*c*2, synthetic material generation process 10*c*3, and synthetic material generation process 10*c*4.

Synthetic material generation process 10*s* may be a server application and may reside on and may be executed by computing device 300, which may be connected to network 302 (e.g., the Internet or a local area network). Examples of computing device 300 may include, but are not limited to: a personal computer, a server computer, a series of server computers, a mini computer, a mainframe computer, a smartphone, or a cloud-based computing platform.

The instruction sets and subroutines of synthetic material generation process 10*s*, which may be stored on storage device 304 coupled to computing device 300, may be executed by one or more processors (not shown) and one or more memory architectures (not shown) included within computing device 300. Examples of storage device 304 may include but are not limited to: a hard disk drive; a RAID device; a random-access memory (RAM); a read-only memory (ROM); and all forms of flash memory storage devices.

Network 302 may be connected to one or more secondary networks (e.g., network 306), examples of which may include but are not limited to: a local area network; a wide area network; or an intranet, for example.

Examples of synthetic material generation processes 10*c*1, 10*c*2, 10*c*3, 10*c*4 may include but are not limited to a web browser, a game console user interface, a mobile device user interface, or a specialized application (e.g., an application running on e.g., the Android™ platform, the iOS™ platform, the Windows™ platform, the Linux™ platform or the UNIX™ platform). The instruction sets and subroutines of synthetic material generation processes 10*c*1, 10*c*2, 10*c*3, 10*c*4, which may be stored on storage devices 308, 310, 312, 314 (respectively) coupled to client electronic devices 316, 318, 320, 322 (respectively), may be executed by one or more processors (not shown) and one or more memory architectures (not shown) incorporated into client electronic devices 316, 318, 320, 322 (respectively). Examples of storage devices 308, 310, 312, 314 may include but are not limited to: hard disk drives; RAID devices; random access memories (RAM); read-only memories (ROM), and all forms of flash memory storage devices.

Examples of client electronic devices 316, 318, 320, 322 may include, but are not limited to a personal digital assistant (not shown), a tablet computer (not shown), laptop computer 316, smart phone 318, smart phone 320, personal computer 322, a notebook computer (not shown), a server computer (not shown), a gaming console (not shown), and a dedicated network device (not shown). Client electronic devices 316, 318, 320, 322 may each execute an operating system, examples of which may include but are not limited to Microsoft Windows™, Android™, iOS™, Linux™, or a custom operating system.

Users 324, 326, 328, 330 may access synthetic material generation process 10 directly through network 302 or through secondary network 306. Further, synthetic material generation process 10 may be connected to network 302 through secondary network 306, as illustrated with link line 332.

The various client electronic devices (e.g., client electronic devices 316, 318, 320, 322) may be directly or indirectly coupled to network 302 (or network 306). For example, laptop computer 316 and smart phone 318 are shown wirelessly coupled to network 302 via wireless communication channels 334, 336 (respectively) established between laptop computer 316, smart phone 318 (respectively) and cellular network/bridge 338, which is shown directly coupled to network 302.

Further, smart phone 320 is shown wirelessly coupled to network 302 via wireless communication channel 340 established between smart phone 320 and wireless access point (i.e., WAP) 342, which is shown directly coupled to network 302. Additionally, personal computer 322 is shown directly coupled to network 306 via a hardwired network connection.

WAP 342 may be, for example, an IEEE 802.11a, 802.11b, 802.11g, 802.11n, Wi-Fi, and/or Bluetooth device that is capable of establishing wireless communication channel 340 between smart phone 320 and WAP 342. As is known in the art, IEEE 802.11x specifications may use Ethernet protocol and carrier sense multiple access with collision avoidance (i.e., CSMA/CA) for path sharing. As is known in the art, Bluetooth is a telecommunications industry specification that allows e.g., mobile phones, computers, and personal digital assistants to be interconnected using a short-range wireless connection.

General

As will be appreciated by one skilled in the art, the present disclosure may be embodied as a method, a system, or a computer program product. Accordingly, the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, the present disclosure may take the form of a computer program product on a computer-usable storage medium having computer-usable program code embodied in the medium.

Any suitable computer usable or computer readable medium may be used. The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium may include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a transmission media such as those supporting the Internet or an intranet, or a magnetic storage device. The computer-usable or computer-readable medium may also be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device. The computer-usable medium may include a propagated data signal with the computer-usable program code embodied therewith, either in baseband or as part of a carrier wave. The computer usable program code may be transmitted using any appropriate medium, including but not limited to the Internet, wireline, optical fiber cable, RF, etc.

Computer program code for carrying out operations of the present disclosure may be written in an object-oriented programming language. However, the computer program code for carrying out operations of the present disclosure may also be written in conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through a local area network/a wide area network/the Internet.

The present disclosure is described with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, may be implemented by computer program instructions. These computer program instructions may be provided to a processor of a general-purpose computer/special purpose computer/other programmable data processing apparatus, such that the instructions, which execute via the processor of the computer or other programmable data processing apparatus, create means for implementing the functions/acts specified in the flowchart and/or block diagram block or blocks.

These computer program instructions may also be stored in a computer-readable memory that may direct a computer or other programmable data processing apparatus to function in a particular manner, such that the instructions stored in the computer-readable memory produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the flowchart and/or block diagram block or blocks.

The flowcharts and block diagrams in the figures may illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, not at all, or in any combination with any other flowcharts depending upon the functionality involved. It will also be noted that each block of the block diagrams and/or flowchart illustrations, and combinations of blocks in the block diagrams and/or flowchart illustrations, may be implemented by special purpose hardware-based systems that perform the specified functions or acts, or combinations of special purpose hardware and computer instructions.

The terminology used herein is for the purpose of describing particular embodiments only and is not intended to be limiting of the disclosure. As used herein, the singular forms “a”, “an” and “the” are intended to include the plural forms as well, unless the context clearly indicates otherwise. It will be further understood that the terms “comprises” and/or “comprising,” when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description but is not intended to be exhaustive or limited to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

A number of implementations have been described. Having thus described the disclosure of the present application in detail and by reference to embodiments thereof, it will be apparent that modifications and variations are possible without departing from the scope of the disclosure defined in the appended claims.

What is claimed is:

1. A computed-implemented method, executed on a computing device, comprising:

accessing a first siloed dataset concerning one or more medical notes;

processing the first siloed dataset to identify clinical items within the one or more medical notes, thus defining a first tagged clinical item set;

selecting a first set of templates for the first siloed dataset based, at least in part, upon the first tagged clinical item set within the first siloed dataset;

defining a first instruct dataset for the first siloed dataset based, at least in part upon the first set of templates and first tagged clinical item set; and training a generative model using the first instruct dataset, thus defining a generative model trained for the first siloed dataset.

2. The computed-implemented method of claim 1 further comprising:

using the generative model trained for the first siloed dataset to generate a first synthetic dataset based, at least in part, upon the first siloed dataset.

3. The computed-implemented method of claim 2 wherein the first synthetic dataset includes one or more synthetic medical notes.

4. The computed-implemented method of claim 2 wherein the first synthetic dataset is a data twin of the first siloed dataset that encompasses the spirit and style of the of the first siloed dataset.

5. The computed-implemented method of claim 1 further comprising:

processing the first siloed dataset to remove personally identifiable information included within the one or more medical notes.

6. The computed-implemented method of claim 1 wherein the first set of templates is chosen from a plurality of predefined templates.

7. The computed-implemented method of claim 1 further comprising:

accessing at least one additional siloed dataset concerning one or more medical notes;

processing the at least one additional siloed dataset to identify clinical items within the one or more medical notes, thus defining at least one additional tagged clinical item set;

selecting at least one additional set of templates for the at least one additional siloed dataset based, at least in part, upon the at least one additional tagged clinical item set within the at least one additional siloed dataset;

defining at least one additional instruct dataset for the at least one additional siloed dataset based, at least in part upon the at least one additional set of templates and the at least one additional tagged clinical item set; and training the generative model using the at least one additional instruct dataset, thus defining a generative model trained for the at least one additional siloed dataset.

8. The computed-implemented method of claim 7 further comprising:

using the generative model trained for the at least one additional siloed dataset to generate at least one additional synthetic dataset based, at least in part, upon the at least one additional siloed dataset.

9. The computed-implemented method of claim 8 wherein the at least one additional synthetic dataset includes one or more synthetic medical notes.

10. The computed-implemented method of claim 8 wherein the at least one additional synthetic dataset is a data twin of the at least one additional siloed dataset that encompasses the spirit and style of the of the at least one additional siloed dataset.

11. The computed-implemented method of claim 7 further comprising:

processing the at least one additional siloed dataset to remove personally identifiable information included within the one or more medical notes.

12. A non-transitory computer program product residing on a computer readable medium having a plurality of instructions stored thereon which, when executed by a processor, cause the processor to perform operations comprising: accessing a first siloed dataset concerning one or more medical notes; processing the first siloed dataset to identify clinical items within the one or more medical notes, thus defining a first tagged clinical item set; selecting a first set of templates for the first siloed dataset based, at least in part, upon the first tagged clinical item set within the first siloed dataset; defining a first instruct dataset for the first siloed dataset based, at least in part upon the first set of templates and first tagged clinical item set; training a generative model using the first instruct dataset, thus defining a generative model trained for the first siloed dataset; and using the generative model trained for the first siloed dataset to generate a first synthetic dataset based, at least in part, upon the first siloed dataset.

13. The computer program product of claim 12 wherein the first synthetic dataset includes one or more synthetic medical notes.

14. The computer program product of claim 12 wherein the first synthetic dataset is a data twin of the first siloed dataset that encompasses the spirit and style of the of the first siloed dataset.

15. The computer program product of claim 12 further comprising:

processing the first siloed dataset to remove personally identifiable information included within the one or more medical notes.

16. The computer program product of claim 12 further comprising:

accessing at least one additional siloed dataset concerning one or more medical notes;

processing the at least one additional siloed dataset to identify clinical items within the one or more medical notes, thus defining at least one additional tagged clinical item set;

selecting at least one additional set of templates for the at least one additional siloed dataset based, at least in part, upon the at least one additional tagged clinical item set within the at least one additional siloed dataset;

defining at least one additional instruct dataset for the at least one additional siloed dataset based, at least in part upon the at least one additional set of templates and the at least one additional tagged clinical item set; and training the generative model using the at least one additional instruct dataset, thus defining a generative model trained for the at least one additional siloed dataset.

17. The computer program product of claim 16 further comprising:

using the generative model trained for the at least one additional siloed dataset to generate at least one additional synthetic dataset based, at least in part, upon the at least one additional siloed dataset.

18. A computing system including a processor and memory configured to perform operations comprising:

accessing a first siloed dataset concerning one or more medical notes;

processing the first siloed dataset to remove personally identifiable information included within the one or more medical notes;

processing the first siloed dataset to identify clinical items within the one or more medical notes, thus defining a first tagged clinical item set;

selecting a first set of templates for the first siloed dataset based, at least in part, upon the first tagged clinical item set within the first siloed dataset;

defining a first instruct dataset for the first siloed dataset based, at least in part upon the first set of templates and first tagged clinical item set;

training a generative model using the first instruct dataset, thus defining a generative model trained for the first siloed dataset; and using the generative model trained for the first siloed dataset to generate a first synthetic dataset based, at least in part, upon the first siloed dataset.

19. The computing system of claim 18 further comprising:

accessing at least one additional siloed dataset concerning one or more medical notes;

processing the at least one additional siloed dataset to identify clinical items within the one or more medical notes, thus defining at least one additional tagged clinical item set;

selecting at least one additional set of templates for the at least one additional siloed dataset based, at least in part, upon the at least one additional tagged clinical item set within the at least one additional siloed dataset;

defining at least one additional instruct dataset for the at least one additional siloed dataset based, at least in part upon the at least one additional set of templates and the at least one additional tagged clinical item set; and training the generative model using the at least one additional instruct dataset, thus defining a generative model trained for the at least one additional siloed dataset.

20. The computing system of claim 19 further comprising:

using the generative model trained for the at least one additional siloed dataset to generate at least one additional synthetic dataset based, at least in part, upon the at least one additional siloed dataset.

* * * * *